United States Patent
Chiu et al.

(10) Patent No.: US 10,717,714 B2
(45) Date of Patent: Jul. 21, 2020

(54) REACTIVE ULTRAVIOLET ABSORBER AND APPLICATION THEREOF

(71) Applicants: CHITEC TECHNOLOGY CO., LTD., Taipei City, Taiwan (CN); Hsiaofen Lung, Taipei (TW)

(72) Inventors: Chingfan Chris Chiu, Taipei (CN); Huang-min Wu, Taipei (CN); Wei-chun Chang, Taipei (CN); Chi-feng Wu, Taipei (CN); Ching-hao Cheng, Taipei (CN); Shao-hsuan Wu, Taipei (CN)

(73) Assignee: CHITEC TECHNOLOGY CO., LTD., Taipei (TW)

( * ) Notice: Subject to any disclaimer, the term of this patent is extended or adjusted under 35 U.S.C. 154(b) by 0 days.

(21) Appl. No.: 16/609,901

(22) PCT Filed: Jul. 7, 2017

(86) PCT No.: PCT/CN2017/092254
§ 371 (c)(1),
(2) Date: Oct. 31, 2019

(87) PCT Pub. No.: WO2019/006750
PCT Pub. Date: Jan. 10, 2019

(65) Prior Publication Data
US 2020/0199084 A1   Jun. 25, 2020

(51) Int. Cl.
| | | |
|---|---|---|
| *C07D 249/20* | (2006.01) | |
| *C08L 75/04* | (2006.01) | |
| *C08G 18/76* | (2006.01) | |
| *C08G 18/32* | (2006.01) | |
| *C08K 5/3475* | (2006.01) | |
| *C08G 18/75* | (2006.01) | |

(52) U.S. Cl.
CPC ....... *C07D 249/20* (2013.01); *C08G 18/3203* (2013.01); *C08G 18/751* (2013.01); *C08G 18/7621* (2013.01); *C08G 18/7664* (2013.01); *C08K 5/3475* (2013.01); *C08L 75/04* (2013.01)

(58) Field of Classification Search
CPC .................................................. C07D 249/20
See application file for complete search history.

(56) References Cited

U.S. PATENT DOCUMENTS 4,926,190 A * 5/1990 Laver ............... D21H 21/30
347/105

* cited by examiner

*Primary Examiner* — Laura L Stockton
(74) *Attorney, Agent, or Firm* — Christensen, Fonder, Dardi & Herbert PLLC

(57) ABSTRACT

A reactive UV absorber suitable for polyurethane is provided. The reactive UV absorber is a compound of formula 1:

[formula 1]

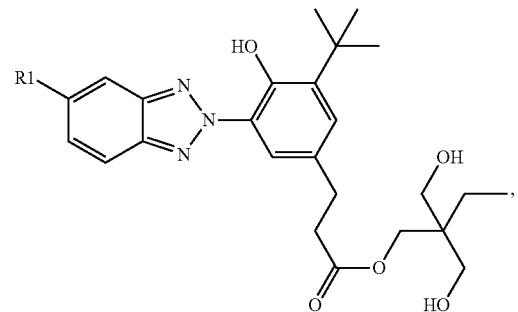

wherein R1 is H or Cl.

7 Claims, No Drawings

REACTIVE ULTRAVIOLET ABSORBER AND APPLICATION THEREOF

PRIORITY CLAIM

The present application is a National Phase entry of PCT Application No. PCT/CN2017/092254, filed Jul. 7, 2017, the disclosure of which is hereby incorporated by reference herein in its entirety.

BACKGROUND OF THE INVENTION

Field of the Invention

The present invention provides a reactive UV absorber and uses of the same. The reactive UV absorber is particularly suitable for use in polyurethane (PU).

Descriptions of the Related Art

Polyurethane is an important type of polymer formed by polymerizing polyols and isocyanates, wherein, by adjusting the ratio of raw materials, it is possible to produce materials with desired mechanical properties, including abrasion resistance, temperature tolerance, flexibility, elongation, etc. Currently, polyurethane is broadly used in various materials such as paints, elastomers, foam materials, adhesives, sealing agents and the like.

A shortcoming of polyurethane is that it easily degrades when irradiated with UV light. Especially in an outdoor setting with strong sunlight, the polyurethane materials degrades even faster. To prevent degradation of polyurethane materials caused by UV light, it is common to have a UV absorber (UVA) physically mixed into polyurethane to resist the adverse effects of UV light. Among the UV absorbers, benzotriazole (BTZ)-type UV absorbers have the best efficacy.

However, the physically-mixed UV absorbers easily undergo migration in polyurethane materials, and further result in the blooming of polyurethane materials or adversely affect the surface properties of polyurethane materials. For example, the surface of the polyurethane materials may become tacky, or products utilizing the same may even fade. Therefore, improving the compatibility of a UV absorber in a polyurethane material to avoid or reduce the occurrence of migration has become an important issue in the development of UV absorbers. Generally, by using the following two methods, the compatibility of a UV absorber in a polyurethane material can be improved to retard or eliminate migration of the UV absorber.

The first method is to increase the molecular weight of an UV absorber, such as the technique disclosed by U.S. Pat. Nos. 4,853,471 and 7,381,762, wherein, by increasing the molecular weight of the UV absorber, the migration rate of the UV absorber molecules in the polyurethane material is reduced. However, this method can only reduce the migration rate but cannot sufficiently avoid the migration. In addition, since increasing the molecular weight of the UV absorber correspondingly reduces the effective amount of the UV absorber, the amount of the UV absorber used must be increased to provide a comparable UV light-resisting effect.

The second method is that a UV absorber is synthesized as a reactive UV absorber, wherein the hydroxyl groups included therein participate in the polymerization reaction carried out during the synthesis of polyurethane such that the UV absorber is directly attached to the structure of the polyurethane by chemical bonds. Examples of such reactive UV absorbers include UV absorbers with the following structures of formula (IIIa) or (IIIb) disclosed by U.S. Pat. No. 5,459,222.

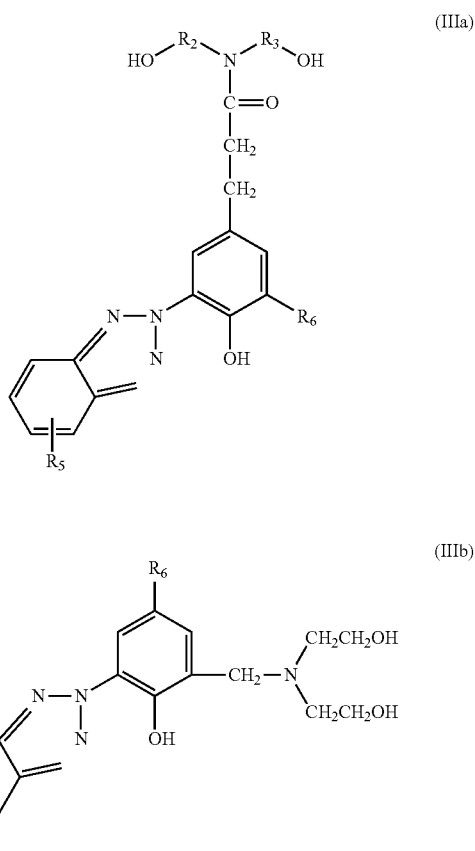

In terms of efficacy, the second method can more effectively solve the problem of migration of the UV absorber. However, the reactive UV absorbers disclosed in the prior art still have disadvantages, such as difficulty in manufacturing, poor thermal stability, and poor compatibility with polyurethane.

SUMMARY OF THE INVENTION

In view of the abovementioned technical problems, the present invention provides a reactive UV absorber, which is a benzotriazole-type UV absorber, that is particularly suitable for application in a polyurethane material, as described below. Since the reactive UV absorber of the present invention is directly attached to the structure of the polyurethane by chemical bonds, it solves the problem of migration of the UV absorber. In addition, the reactive UV absorber of the present invention has advantages in that the thermal stability is good, the UV light-resisting effect is excellent, the manufacturing method thereof is simpler and the absorber is easier to purify.

An objective of the present invention is to provide a reactive UV absorber, which is represented by the following formula 1:

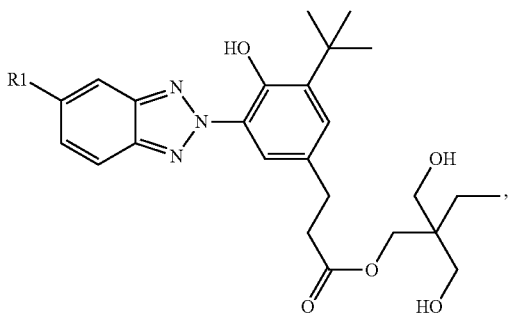

[formula 1]

wherein R1 is H or Cl.

Another objective of the present invention is to provide a polyurethane precursor composition, comprising:
(a) a polyol;
(b) a polyisocyanate; and
(c) the aforementioned reactive UV absorber,
wherein, based on the total weight of component (a), component (b) and component (c), the amount of the reactive UV absorber is about 0.1 wt % to about 50 wt %, such as about 0.5 wt % to about 10 wt %.

In some embodiments of the present invention, the polyol in the polyurethane precursor composition may be selected from the group consisting of ethylene glycol, 1,2-propylene glycol, 1,3-propylene glycol, 1,2-butylene glycol, 1,3-butylene glycol, 1,4-butylene glycol, glycerol, trimethylolpropane, pentaerythritol, polycarbonate polyols, polyacrylate polyols, polyether polyols, polyester polyols, and combinations thereof.

In some embodiments of the present invention, the polyisocyanate in the polyurethane precursor composition may be selected from the group consisting of toluene diisocyanate (TDI), methylene diphenyl diisocyanate (MDI), hexamethylene diisocyanate (HDI), cyclohexyl diisocyanate (CHDI), tetramethylxylene diisocyanate (TMXDI), hydrogenated m-xylene diisocyanate ($H_6$XDI), isophorone diisocyanate (IPDI), dicyclohexylmethane 4,4'-diisocyanate (HMDI); biurets, dimers and trimers, and prepolymers thereof and combinations thereof.

In some embodiments of the present invention, the aforementioned polyurethane precursor composition may further comprise a component selected from the group consisting of a solvent, a catalyst, an antioxidant, a filler, a compatibilizer, a flame retardant, a heat stabilizer, a light stabilizer, a metal deactivator, a plasticizer, a lubricant, an emulsifier, a dye, a pigment, a brightener, an anti-static agent, a foaming agent, a chain extender, an anti-hydrolysis agent, a surfactant, a cross-linking agent, a photoinitiator, a pH regulator, an adhesion promoter, a germicide, and combinations thereof. The chain extender is, for example, a hydrophilic-type chain extender selected from the group consisting of dimethylolpropionic acid (DMPA), dimethylolbutanoic acid (DMBA), and combinations thereof.

Another objective of the present invention is to provide a polyurethane resistant to the harmful effects of UV light, which is prepared by subjecting the aforementioned polyurethane precursor composition to polymerization reaction.

Another objective of the present invention is to provide a polyurethane product, which comprises the aforementioned polyurethane and is provided in the form of a fiber, a paint, an elastomer, a foam material, an adhesive or a sealing agent.

Another objective of the present invention is to provide a method for resisting the harmful effects of UV light, comprising the use of the aforementioned polyurethane.

To render the above objectives, technical features and advantages of the present invention more apparent, the present invention will be described in detail with reference to some embodiments hereinafter.

BRIEF DESCRIPTION OF THE DRAWINGS

Not applicable.

DESCRIPTION OF THE PREFERRED EMBODIMENT

Hereinafter, some embodiments of the present invention will be described in detail. However, without departing from the spirit of the present invention, the present invention may be embodied in various embodiments and should not be considered to be limited to those described in the specification. In addition, unless it is additionally explained, the expressions "a," "the," or the like recited in the specification (especially in the claims) should include both the singular and the plural forms.

Reactive UV Absorber

It has been found from research that a benzotriazole compound can be synthesized by a simple method. The benzotriazole compound has at least the following advantages: the compound has good hydrolysis resistance and is in the form of a polyol, such that it can be used as a hydrolysis-resisting reactive UV absorber; the compound is alkaline and with excellent solubility in alcohols and polyols, which are main components of polyurethane. Due to these properties, it is particularly suitable for being a UV absorber in polyurethane applications; finally, the compound has good thermal stability and is able to provide an excellent UV light-resisting effect.

Specifically, the reactive UV absorber of the present invention is represented by formula 1:

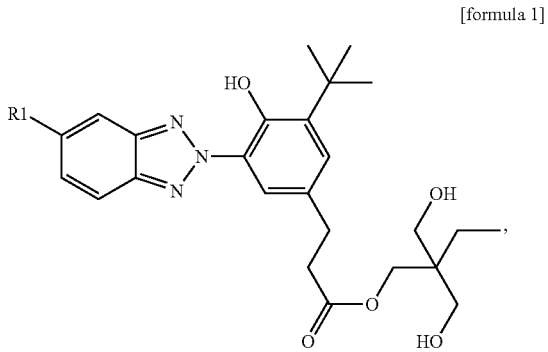

[formula 1]

wherein R1 is H or Cl.

The synthesis method of the compound represented by formula 1 will be described in the examples below and is not described here.

Polyurethane Precursor Composition

As described above, the reactive UV absorber of the present invention is particularly suitable for use in polyurethane materials. Therefore, the present invention also provides a polyurethane precursor composition, which comprises (a) a polyol, (b) a polyisocyanate, and (c) the reactive UV absorber of the present invention, wherein component (a) and component (b) are major components for forming a polyurethane, and component (c) is a component that provides the polyurethane with the ability to resist the harmful effects of UV light.

Component (a) may be monomers, oligomers, or polymers of an alcohol with at least two hydroxyl groups, or mixtures thereof that are known to be able to be used in the preparation of a polyurethane. Examples of polyol monomers include but are not limited to ethylene glycol, 1,2-propylene glycol, 1,3-propylene glycol, 1,2-butylene glycol, 1,3-butylene glycol, 1,4-butylene glycol, glycerol, trimethylolpropane, pentaerythritol, and mixtures thereof. Examples of oligomers or polymers of polyols include but are not limited to polycarbonate polyols, polyacrylate polyols, polyether polyols, polyester polyols, and mixtures thereof, such as being selected from the group consisting of polyacrylate diols, polyether diols, polyester diols, and mixtures thereof.

Component (b) may be monomers, additive products, dimers or trimers, prepolymers of an isocyanate with at least two isocyanate groups, or mixture thereof that are known to be able to be used in the preparation of a polyurethane, wherein the additive products are, for example, additive products of an isocyanate monomer and an alcohol or an amine. Examples of polyisocyanate that can be used in the present invention include but are not limited to toluene diisocyanate (TDI), methylene diphenyl diisocyanate (MDI), hexamethylene diisocyanate (HDI), cyclohexyl diisocyanate (CHDI), tetramethylxylene diisocyanate (TMXDI), hydrogenated m-xylylene diisocyanate ($H_6XDI$), isophorone diisocyanate (IPDI), dicyclohexylmethane 4,4'-diisocyanate (HMDI); biurets, dimers and trimers, and prepolymers thereof; and combinations thereof.

In the polyurethane precursor composition of the present invention, the proportions of component (a), component (b) and component (c) are generally not particularly limited. Persons having ordinary skill in the art can rely on their common skill and the description of the present specification to adjust the proportion depending on the situation, such as the desired properties of the polyurethane material, the types of the polyol and the polyisocyanate, and the required UV light-resisting effect. Generally, based on the total weight of component (a), component (b) and component (c), the amount of component (c) (the reactive UV absorber) is about 0.1 wt % to about 50 wt %, such as 0.5 wt %, 1 wt %, 1.5 wt %, 2 wt %, 3 wt %, 5 wt %, 7 wt %, 10 wt %, 15 wt %, 20 wt %, 25 wt %, 30 wt %, 35 wt %, or 40 wt %. In some embodiments of the present invention, based on the total weight of component (a), component (b) and component (c), the amount of component (c) is about 0.5 wt % to about 10 wt %.

In addition to components (a), (b) and (c), the polyurethane precursor composition of the present invention may further comprise other optional components to improve the processability of the polyurethane precursor composition during the manufacturing process of polyurethane, improve the polymerization reaction, or improve the targeted properties of the polyurethane material. Examples of such optional components include but are not limited to a solvent, a catalyst, an antioxidant, a filler, a compatibilizer, a flame retardant, a heat stabilizer, a light stabilizer, a metal deactivator, a plasticizer, a lubricant, an emulsifier, a dye, a pigment, a brightener, an anti-static agent, a foaming agent, a chain extender, an anti-hydrolysis agent, a surfactant, a cross-linking agent, a photoinitiator, a pH regulator, an adhesion promoter, and a germicide. Each of the components can either be used alone or in any combination.

In some embodiments of the present invention, to improve the hydrophilic property of the prepared polyurethane, the polyurethane precursor composition further comprises a hydrophilic-type chain extender selected from the group consisting of dimethylolpropionic acid (DMPA), dimethylolbutanoic acid (DMBA), and combinations thereof. In addition, to improve the reaction of isocyanate groups and hydroxyl groups, the polyurethane precursor composition further comprises a catalyst. Catalysts suitable for synthesizing a polyurethane are the ones well known by those skilled in the art, wherein the examples thereof include but are not limited to tertiary amine and a metal catalyst containing tin, zinc, cobalt or manganese, wherein the metal catalyst is, for example, dimethyltin dilaurate, dibutyltin dilaurate, or dioctyltin dilaurate. The amount of the catalyst is not particularly limited as long as it is able to provide the desired catalytic effect. Generally, based on the total weight of the components (a), (b), (c) and the catalyst, the amount of the catalyst is about 0.001 wt % to about 10 wt %, such as 0.005 wt %, 0.01 wt %, 0.02 wt %, 0.05 wt %, 0.1 wt %, 0.5 wt %, 1 wt %, 2 wt %, or 5 wt %.

Polyurethane Resistant to the Harmful Effects of UV Light and Uses of the Same

The polyurethane precursor composition of the present invention can be used to form a polyurethane material by, for example, melt polymerization or solution polymerization. As verified in the examples below, the polyurethane material of the present invention has excellent stability due to the fact that it comprises a moiety formed by the reaction in which component (c) participates. The polyurethane material of the present invention does not manifest the problems of precipitation of the UV absorber or blooming of the material even after being stored at normal temperature and normal pressure for a long period of time. In addition, the polyurethane material of the present invention has excellent UV light-resisting ability. To prepare the polyurethane of the present invention using polymerization, persons having ordinary skill in the art can rely on their common skill and the description of the present specification to complete the polymerization. Relevant examples of polymerization are provided in the examples below and are not described here.

In the present invention, various polyurethane products can be made by, for example, adjusting the types of the polyol and the polyisocyanate in the polyurethane precursor composition, wherein the polyurethane products are products such as fibers, paints, elastomers, foam materials, adhesives or sealing agents. For example, with respect to application in the textile industry, polyether diols can be used as the component (a) and diisocyanate can be used as the component (b) to prepare a prepolymer. A diamine (such as ethylenediamine) can be used to extend the chain to prepare elastic fibers (such as Spandex fibers) that can be used in the textile industry.

As shown in the experimental results of the examples below, the polyurethane of the present invention has an excellent UV light-resisting effect. Therefore, the polyurethane of the present invention can be used as a technical means for resisting UV light to provide a method for resisting the harmful effects of UV light. For example, the polyurethane of the present invention can be used directly as the material or part of the material for a specific product to provide the product with the function of UV light resistance. Alternatively, the polyurethane material of the present invention can be used to cover the surface of an object that needs to be protected. For example, the polyurethane is made into a paint, and then the paint is coated on the surface of an object to form a protective barrier on the surface that blocks the UV light. However, the present invention does not exclude cases where the polyurethane material is used in other ways to resist the harmful effects of UV light.

The present invention is further illustrated by the following specific examples.

EXAMPLES

Preparation Example 1: Synthesis of Reactive UV Absorber I

A 1 L three-necked flask was prepared, 106 g of 3-(2H-benzotriazol-2-yl)-5-(1,1-dimethylethyl)-4-hydroxy-benzenepropanoic acid (CAS #84268-36-0), 162 g of trimethylolpropane (CAS #77-99-6), 1.0 g of p-toluenesulfonic acid (PTSA, CAS #104-15-4) and 500 g of toluene were added in sequence thereto at room temperature and stirred evenly. The mixture was heated to 110° C., refluxed to remove water for 3 hours, and reacted. After the reaction was confirmed complete by High Performance Liquid Chromatography (HPLC), the reaction product was extracted once each with 300 g and 200 g of pure water. The organic layer was collected, cooled and filtered to collect the solid product. The solid product was dried at 90° C. to 100° C. to obtain the reactive UV absorber I with the structure of formula 1 (wherein R1 is H). The yield was calculated to be 80%. The reactive UV absorber I was subjected to nuclear magnetic resonance analysis, and the results are as follows:

1H NMR (CDCl3, 500 MHz) δ=11.80 (s, 1H), 8.13 (d, J=2.5 Hz, 1H), 7.92-7.94 (m, 2H), 7.4-87.50 (m, 2H), 7.21 (d, J=2.5 Hz, 1H), 4.22 (s, 2H), 3.48-3.53 (m, 4H), 3.01 (t, J=7.5 Hz, 2H), 2.77 (t, J=7.5 Hz, 2H), 2.72 (t, J=6.0 Hz, 2H), 1.64 (s, 9H), 1.20-1.23 (m, 2H), 0.81 (t, J=8.0 Hz, 3H)

13C NMR (d6-DMSO, 75.5 MHz) δ=7.3, 21.6, 29.3, 29.7, 35.0, 35.1, 42.4, 60.9, 64.2, 117.6, 119.4, 125.6, 128.0, 131.4, 138.6, 142.5, 146.6, 172.2

Preparation Example 2: Synthesis of Reactive UV Absorber II

The synthetic steps of reactive UV absorber I were repeated to prepare reactive UV absorber II with the structure of formula 1 (wherein R1 is Cl), except that 3-(2H-benzotriazol-2-yl)-5-(1,1-dimethylethyl)-4-hydroxy-benzenepropanoic acid was replaced by 128 g of 3-(5-chloro-2H-benzotriazol-2-yl)-5-(1,1-dimethylethyl)-4-hydroxy-benzenepropanoic acid (CAS #83573-67-5) as a reactant. The yield of the reactive UV absorber II was 82%. The reactive UV absorber II was subjected to nuclear magnetic resonance analysis, and the results are as follows:

1H NMR (CDCl3, 300 MHz) δ=11.56 (s, 1H), 8.09 (d, J=2.1 Hz, 1H), 7.86-7.93 (m, 2H), 7.44 (dd, J=1.8, 9.0 Hz, 1H), 7.22 (d, J=2.1 Hz, 1H), 4.22 (s, 2H), 3.44-3.56 (m, 4H), 3.01 (t, J=7.5 Hz, 2H), 2.76 (t, J=7.5 Hz, 2H), 2.65 (t, J=6.0 Hz, 2H), 1.49 (s, 9H), 1.18-1.25 (m, 2H), 0.84 (t, J=8.1 Hz, 3H)

Example 1: Solubility Test

The reactive UV absorber I and the comparative reactive UV absorber A represented by the following formula A (an embodiment of reactive UV absorber with formula (IIIa) disclosed by U.S. Pat. No. 5,459,222) were each separately added gram by gram into a 100 ml solvent and then sufficiently stirred and oscillated. The dissolution of the reactive UV absorber was observed under visual inspection until the added reactive UV absorber was no longer dissolved. The solubility of the reactive UV absorber I of the present invention and that of the comparative reactive UV absorber A were thus compared for different solvents, and the results are shown in the following Table 1.

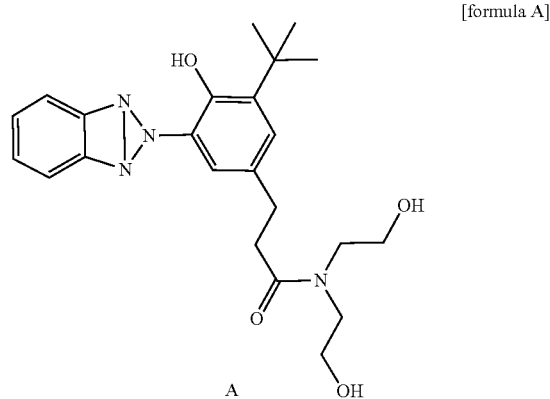

[formula A]

TABLE 1

| | Solubility Test Results | |
|---|---|---|
| | UV absorber | |
| Solvent | Reactive UV absorber I (g) | Comparative reactive UV absorber A (g) |
| Methanol | 10.0 | 3.0 |
| Isopropanol | 7.5 | 1.0 |
| Xylene | 1.5 | Insoluble (<0.01) |

As shown in Table 1, the reactive UV absorber I of the present invention clearly has higher solubility in various solvents compared to the comparative UV absorber A. The reactive UV absorber I of the present invention with excellent solubility in alcohols and polyols, which are main components for preparing a polyurethane, the reactive UV absorber I of the present invention will have better compatibility with the polyurethane precursor.

Example 2: Thermal Stability Test 2 g each of the reactive UV absorber I of the present invention, the comparative reactive UV absorber A, and the comparative reactive UV absorber B represented by the following formula B (an embodiment of reactive UV absorber with formula (IIIb) disclosed by U.S. Pat. No. 5,459,222) were respectively dissolved in 10 ml of dimethylformamide (DMF), and the obtained dimethylformamide solutions were subjected to thermal processing at 150° C. for 3 hours. The Gardner color scales of the solutions were measured by colorimeter (Lovibond PFXi-195). The changes in color (delta color) before and after thermal processing were calculated and the results are shown in the following Table 2.

[formula B]

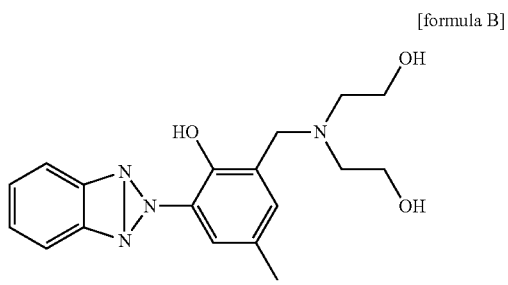 [SMILES: Cc1cc(CN(CCO)CCO)c(O)c(-n2n3c4ccccc4n23)c1]

TABLE 2

The Changes in Color Before and After Heating at 150° C. for 3 Hours

| Color | UV absorber | | |
|---|---|---|---|
| | Reactive UV absorber I | Comparative reactive UV absorber A | Comparative reactive UV absorber B |
| Initial | 3.0 | 5.4 | 4.2 |
| After thermal processing for 3 hours | 4.5 | 9.1 | 7.2 |
| Change in color | 1.5 | 3.7 | 3.0 |

As shown in Table 2, the reactive UV absorber I of the present invention has the lowest initial color such that it has the least influence on the color of the polyurethane material utilizing the same. In addition, the reactive UV absorber I of the present invention has the smallest change in color after being subjected to thermal processing for 3 hours, which shows that the reactive UV absorber I of the present invention has better thermal stability and therefore, will have better stability during the synthesis of the polyurethane.

Example 3: Precipitation Test (Migration Test)

[Thermoplastic Polyurethane A: Without Adding UV Absorber]

133.5 g of PEBA2000 (available from Headway Group; OH value of 56.1), 16.5 g of 1,4-butylene glycol, and 200 ppm of dibutyltin dilaurate were added into a reaction pot and heated to 110° C. Additionally, 66.8 g of methylene diphenyl diisocyanate (MDI) was preheated to 110° C., added to the reaction pot and stirred for 3 minutes for reaction. After the reaction was complete, a thermoplastic polyurethane (TPU) plastic block was obtained. The plastic block was poured out of the reaction pot, pressed into a flat plate while it was hot, and put into an oven to bake at 70° C. for 24 hours to obtain a thermoplastic polyurethane A as the control group.

The thermoplastic polyurethane A was kept at a temperature of 80° C. for 1 hour, and then subjected to mixing by using Brabender plastograph at 175° C. and a spinning rate of 100 rpm for 2 minutes and then released. 20 g of the mixed thermoplastic polyurethane A were placed on a hot press molding machine (available from Long Chang Mechanical Industrial Co., LTD.) and subjected to hot pressing at a pressure of 80 kg/cm' and a temperature of 185° C. for 1.5 minutes. After that, the hot press molded thermoplastic polyurethane A was placed on a cold press machine, cooled for 5 to 10 minutes at a pressure of 50 kg/cm' and pressed into a mold (sized at 14 cm×14 cm×0.07 cm) to finish the preparation of a sample of thermoplastic polyurethane A.

The sample of thermoplastic polyurethane A was kept at normal temperature and normal pressure for several days. The color change of the sample was observed and served as the control group for the precipitation test, and the results are shown in Table 3.

[Thermoplastic Polyurethane B1: Adding 1 wt % of the Reactive UV Absorber I]

The preparation method of thermoplastic polyurethane A was repeated to prepare thermoplastic polyurethane B1, except that the amount of MDI was adjusted to be 63.8 g and 2.2 g of the reactive UV absorber I was added thereto for reaction, to obtain a thermoplastic polyurethane B1 containing about 1 wt % of the reactive UV absorber I.

The method for preparing the sample of thermoplastic polyurethane A was repeated to prepare the sample of thermoplastic polyurethane B1, and then the sample was subjected to the precipitation test. The color change of the sample was observed and the results are shown in Table 3.

[Thermoplastic Polyurethane B2: Adding 5 wt % of the Reactive UV Absorber I]

The preparation method of thermoplastic polyurethane A was repeated to prepare thermoplastic polyurethane B2, except that the amount of MDI was adjusted to be 68.5 g and the amount of the reactive UV absorber I was adjusted to be 11.0 g, to obtain a thermoplastic polyurethane B2 containing about 5 wt % of the reactive UV absorber I.

The method for preparing the sample of thermoplastic polyurethane A was repeated to prepare the sample of thermoplastic polyurethane B2 and then the sample was subjected to the precipitation test. The color change of the sample was observed and the results are shown in Table 3.

[Thermoplastic Polyurethane C1: Adding 1 wt % of Non-Reactive UV Absorber]

The thermoplastic polyurethane A was kept at the temperature of 80° C. for 1 hour, and then the thermoplastic polyurethane A and a non-reactive UV absorber Chiguard 234 were mixed in a weight ratio of 99:1. The mixture was placed in the Brabender plastograph, subjected to mixing at 175° C. and a spinning rate of 100 rpm for 2 minutes, and then released to provide a thermoplastic polyurethane C1 formulation. 20 g of the mixed thermoplastic polyurethane C1 formulation were placed on a hot press molding machine (available from Long Chang Mechanical Industrial Co., LTD.) and subjected to hot pressing at a pressure of 80 kg/cm' and a temperature of 185° C. for 1.5 minutes. After that, the hot press molded thermoplastic polyurethane C1 was placed on a cold press machine, cooled for 5 to 10 minutes at a pressure of 50 kg/cm' and pressed into a mold (sized at 14 cm×14 cm×0.07 cm) to obtain a sample of thermoplastic polyurethane C1 containing 1 wt % of the non-reactive UV absorber.

The sample of thermoplastic polyurethane C1 was kept at normal temperature and normal pressure for several days. The precipitation test was performed by observing the color change of the sample, and the results are shown in Table 3.

[Thermoplastic Polyurethane C2: Adding 2 wt % of Non-Reactive UV Absorber]

The method for preparing the sample of thermoplastic polyurethane C1 was repeated to prepare the sample of thermoplastic polyurethane C2, except that weight ratio of the thermoplastic polyurethane A and the non-reactive UV absorber Chiguard 234 was adjusted to be 98:2 to obtain the sample of thermoplastic polyurethane C2 containing 2 wt % of the non-reactive UV absorber.

The sample of thermoplastic polyurethane C1 was kept at normal temperature and normal pressure for several days.

The precipitation test was performed by observing the color change of the sample, and the results are shown in Table 3.

TABLE 3

Precipitation Test Results

| Testing time | Thermoplastic polyurethane A (control group) | Thermoplastic polyurethane B1 | Thermoplastic polyurethane B2 | Thermoplastic polyurethane C1 | Thermoplastic polyurethane C2 |
|---|---|---|---|---|---|
| 3 days | Transparent | Transparent | Transparent | Transparent | Precipitated (blooming) |
| 5 days | Transparent | Transparent | Transparent | Precipitated (blooming) | — |
| 14 days | Transparent | Transparent | Transparent | — | — |

As shown in Table 3, the samples using the physically mixed non-reactive UV absorber Chiguard 234 both exhibit precipitation. The embodiment with 2 wt % of non-reactive UV absorber added manifested precipitation after only being kept at normal temperature and normal pressure for 3 days, with blooming occurring at the surface of the material. In contrast, the samples of the thermoplastic polyurethane (thermoplastic polyurethane B1 and B2) using the reactive UV absorber of the present invention do not manifest precipitation and the material remain consistently transparent even when a high proportion (about 5 wt %) of the reactive UV absorber I was added. The results show that the thermoplastic polyurethane using the reactive UV absorber of the present invention can have better stability.

Example 4: Aging Test

[Aqueous Polyurethane A: Without Adding UV Absorber]

66 g of isophorone diisocyanate (IPDI), 98 g of polytetrahydrofuran glycol (Mw=2000), 98 g of poly(ethylene adipate) glycol (Mw=2000), 18 g of 2,2-dimethylol propionic acid (DMPA), 100 g of acetone, and 200 ppm of dibutyltin dilaurate catalyst were placed into a reaction flask. After reacting at 55° C. for 5 hours, 13 g of triethylamine and 507 g of water were added thereto and stirred vigorously. After that, 3.5 g of ethylenediamine was added as the chain extender. Lastly, reduced pressure distillation was performed to remove the acetone, and aqueous polyurethane A was obtained.

An aging test was performed on the aqueous polyurethane A by the following method. The aqueous polyurethane A was coated on a glass sheet by an adjustable coater (ERICHSEN multicator model 411) to form a dry film with a thickness of 35 After that, as per the method of ISO 11341, the dry film was exposed to an artificially accelerated aging tester and irradiated with UV light for 1500 hours. The yellowness difference ($\Delta YI$) and the color difference ($\Delta E$) during UV light irradiation were measured and the results are shown in Table 4.

[Aqueous Polyurethane B1: Adding 0.5 wt % of the Reactive UV Absorber I]

The preparation method of aqueous polyurethane A was repeated to prepare aqueous polyurethane B1, except that 1.4 g of the UV absorber I was added additionally thereto for reaction, to obtain an aqueous polyurethane B1 containing about 0.5 wt % of the reactive UV absorber I based on the polyurethane component.

The testing method of aqueous polyurethane A was repeated to perform an aging test on the aqueous polyurethane B1, and the results are shown in Table 4.

[Aqueous Polyurethane B2: Adding 1 wt % of the Reactive UV Absorber I]

The preparation method of aqueous polyurethane A was repeated to prepare aqueous polyurethane B2, except that the amount of DMPA was adjusted to be 16.6 g and also 2.8 g of the reactive UV absorber I was added thereto for reaction, to obtain a aqueous polyurethane B2 containing about 1 wt % of the reactive UV absorber I based on the polyurethane component.

The testing method of aqueous polyurethane A was repeated to perform an aging test on the aqueous polyurethane B2, and the results are shown in Table 4.

[Aqueous Polyurethane C: Adding 1 wt % of Non-Reactive UV Absorber]

280.4 g of the aqueous polyurethane A and 1 g of a non-reactive UV absorber Chiguard 5530 were mixed and stirred evenly to prepare an aqueous polyurethane C containing about 1 wt % of the non-reactive UV absorber based on the polyurethane component.

The testing method of aqueous polyurethane A was repeated to perform an aging test on the aqueous polyurethane C, and the results are shown in Table 4.

TABLE 4

Aging Test Results

| UV light irradiation time | | Aqueous polyurethane A | Aqueous polyurethane B1 | Aqueous polyurethane B2 | Aqueous polyurethane C |
|---|---|---|---|---|---|
| 48 hours | $\Delta YI$ | 0.07 | 0.02 | 0.00 | 0.01 |
| | $\Delta E$ | 0.09 | 0.09 | 0.07 | 0.07 |
| 113 hours | $\Delta YI$ | 0.64 | 0.09 | 0.00 | 0.02 |
| | $\Delta E$ | 0.38 | 0.12 | 0.10 | 0.10 |
| 185 hours | $\Delta YI$ | Whitening | 0.15 | 0.13 | 0.12 |
| | $\Delta E$ | | 0.34 | 0.38 | 0.35 |
| 480 hours | $\Delta YI$ | — | 0.62 | 0.40 | 0.42 |
| | $\Delta E$ | — | 0.67 | 0.66 | 0.67 |
| 700 hours | $\Delta YI$ | — | 1.62 | 0.33 | Whitening |
| | $\Delta E$ | — | 1.31 | 0.68 | |
| 1000 hours | $\Delta YI$ | — | Whitening | 0.77 | — |
| | $\Delta E$ | — | | 0.72 | — |
| 1500 hours | $\Delta YI$ | — | — | 1.57 | — |
| | $\Delta E$ | — | — | 1.20 | — |

As shown in Table 4, the aqueous polyurethane without adding UV absorber clearly has a faster aging rate, and whitening occurs after only 185 hours of UV light irradiation. In addition, with respect to embodiments with added UV absorbers, the aqueous polyurethane B1, which contains about 0.5 wt % of the reactive UV absorber of the present invention based on the polyurethane component, clearly has a slower aging rate than the aqueous polyurethane C, which contains about 1 wt % of the non-reactive UV absorber based on the polyurethane component. The aging rate of the aqueous polyurethane B2, which contains about 1 wt % of the reactive UV absorber of the present invention based on the polyurethane component, is drastically reduced, and whitening does not occur even after 1500 hours of UV light irradiation. The results above show that the reactive UV absorber of the present invention can provide an excellent anti-aging effect to the polyurethane system.

The above examples are used to illustrate the principle and efficacy of the present invention and show the inventive features thereof. People skilled in this field may proceed with a variety of modifications and replacements based on the disclosures and suggestions of the invention as described without departing from the principle and spirit thereof. Therefore, the scope of protection of the present invention is that as defined in the claims as appended.

BRIEF DESCRIPTION OF REFERENCE NUMERALS

Not applicable.

What is claimed is:

1. A reactive UV absorber, which is represented by the following formula 1:

[formula 1]

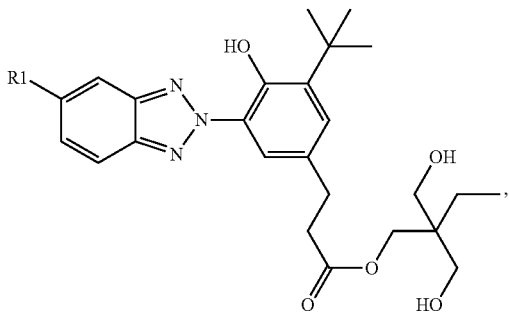

wherein R1 is H or Cl.

2. A polyurethane precursor composition, comprising:
(a) a polyol;
(b) a polyisocyanate; and
(c) the reactive UV absorber of claim 1,
wherein an amount of the reactive UV absorber is about 0.1 wt % to about 50 wt % based on the total weight of component (a), component (b) and component (c).

3. The polyurethane precursor composition of claim 2, wherein the amount of the reactive UV absorber is about 0.5 wt % to about 10 wt % based on the total weight of component (a), component (b) and component (c).

4. The polyurethane precursor composition of claim 2, wherein the polyol is selected from the group consisting of ethylene glycol, 1,2-propylene glycol, 1,3-propylene glycol, 1,2-butylene glycol, 1,3-butylene glycol, 1,4-butylene glycol, glycerol, trimethylolpropane, pentaerythritol, polycarbonate polyols, polyacrylate polyols, polyether polyols, polyester polyols, and combinations thereof.

5. The polyurethane precursor composition of claim 2, wherein the polyisocyanate is selected from the group consisting of toluene diisocyanate (TDI), methylene diphenyl diisocyanate (MDI), hexamethylene diisocyanate (HDI), cyclohexyl diisocyanate (CHDI), tetramethylxylene diisocyanate (TMXDI), hydrogenated m-xylylene diisocyanate ($H_6XDI$), isophorone diisocyanate (IPDI), dicyclohexylmethane 4,4'-diisocyanate (HMDI); biurets, dimers and trimers, and prepolymers thereof and combinations thereof.

6. The polyurethane precursor composition of claim 2, further comprising a component selected from the group consisting of a solvent, a catalyst, an antioxidant, a filler, a compatibilizer, a flame retardant, a heat stabilizer, a light stabilizer, a metal deactivator, a plasticizer, a lubricant, an emulsifier, a dye, a pigment, a brightener, an anti-static agent, a foaming agent, a chain extender, an anti-hydrolysis agent, a surfactant, a cross-linking agent, a photoinitiator, a pH regulator, an adhesion promoter, a germicide, and combinations thereof.

7. The polyurethane precursor composition of claim 6, wherein the chain extender is a hydrophilic-type chain extender selected from the group consisting of dimethylolpropionic acid (DMPA), dimethylolbutanoic acid (DMBA), and combinations thereof.

* * * * *